(12) United States Patent
Lin

(10) Patent No.: US 9,622,649 B2
(45) Date of Patent: *Apr. 18, 2017

(54) ENDOSCOPE WITH A T-SHAPED FLEXIBLE CIRCUIT BOARD

(71) Applicant: AMBU A/S, Ballerup (DK)

(72) Inventor: Rung-De Lin, Taichung (TW)

(73) Assignee: AMBU A/S, Ballerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/228,197

(22) Filed: Mar. 27, 2014

(65) Prior Publication Data

US 2014/0210976 A1 Jul. 31, 2014

Related U.S. Application Data

(63) Continuation-in-part of application No. 13/566,850, filed on Aug. 3, 2012.

(30) Foreign Application Priority Data

Aug. 5, 2011 (TW) .............................. 100214506 U

(51) Int. Cl.
| | | |
|---|---|---|
| A61B 1/04 | (2006.01) | |
| A61B 1/06 | (2006.01) | |
| A61B 1/00 | (2006.01) | |
| A61B 1/05 | (2006.01) | |
| G02B 23/24 | (2006.01) | |

(52) U.S. Cl.
CPC .............. *A61B 1/04* (2013.01); *A61B 1/0011* (2013.01); *A61B 1/051* (2013.01); *A61B 1/0676* (2013.01); *A61B 1/0684* (2013.01); *G02B 23/2476* (2013.01)

(58) Field of Classification Search
CPC ....... A61B 1/05; A61B 1/051; A61B 1/00105; H04N 5/2252; H04N 5/2253; H04N 5/2251; H04N 5/2254; H04N 5/2256; G02B 23/2476; G02B 23/2484
See application file for complete search history.

(56) References Cited

U.S. PATENT DOCUMENTS

| | | |
|---|---|---|
| 8,216,127 B2 | 7/2012 | Zifeng et al. |
| 2008/0231723 A1 | 9/2008 | Yonemitsu et al. |
| 2009/0105538 A1 | 4/2009 | Van Dam et al. |
| 2009/0322867 A1 | 12/2009 | Carrey et al. |
| 2010/0185052 A1 | 7/2010 | Chang |
| 2011/0118549 A1* | 5/2011 | Han .............................. 600/109 |
| 2011/0263942 A1 | 10/2011 | Chen |
| 2013/0271588 A1* | 10/2013 | Kirma et al. ................... 348/76 |

* cited by examiner

*Primary Examiner* — Alexandra Newton
(74) *Attorney, Agent, or Firm* — Faegre Baker Daniels LLP

(57) ABSTRACT

An endoscope with a T-shaped flexible circuit board includes: a base mounting frame, a flexible circuit, a photosensitive element, two light emitting elements and a camera. The photosensitive element, the two light emitting elements and the camera are mounted onto the T-shaped flexible circuit board, then the flexible circuit board deforms to fit in the base mounting frame. During assembly, the photosensitive element, the two light emitting elements and the camera are maintained in the same orientation, and the T-shaped flexible circuit can be pushed into the base mounting frame simply by applying a force in a single direction parallel to the orientation direction of the photosensitive element, the two light emitting elements and the camera.

15 Claims, 7 Drawing Sheets

ENDOSCOPE WITH A T-SHAPED FLEXIBLE CIRCUIT BOARD

This application is a continuation in part of U.S. patent application Ser. No. 13/566,850, which claims the benefit of the earlier filing date of Aug. 3, 2012. Claim 1 of this application is revised from claim 1 of U.S. patent application Ser. No. 13/566,850, claim 2 of this application corresponds to claim 2 of U.S. patent application Ser. No. 13/566,850, and claim 3 is new.

BACKGROUND OF THE INVENTION

Field of the Invention

The present invention relates to an endoscope, and more particularly to an endoscope with a T-shaped flexible circuit board.

Description of the Prior Art

FIG. 1 shows a conventional endoscope 10 which comprises a pipe 11, a camera 12, a light shield 13 and a plurality of LED (light emitting diode) elements 14 mounted on a circuit board 15 and located around the periphery of the camera 12. The light shield 13 is located at the front of the camera 12 to block light. The camera 12 is combined with the light shield 13 and the LED elements 14 and then disposed in the pipe 11, and the pipe 11 is used to insert in a patient's body cavity.

The endoscope 10 is very small and compact in order to insert into the body cavity, hence, it is very difficult to assemble these parts, including the camera 12, the light shield 13, the LED elements 14 and the circuit board 15 together into such a small pipe 11.

On the other hand, the LED elements 14 and the circuit board 15 have to be arranged around the camera 12, and the conventional circuit board 15 is usually made of rigid metal. Hence, arranging the circuit board 15 around the camera 12 would increase the volume of the endoscope 10.

FIGS. 2 and 3 show another endoscope A which a lower housing A1, an upper housing A2, a circuit board A3, a lens A4 and a light source A5. Each of the lower and upper housings A1, A2 is provided with an opening A11, A21 which open in a vertical direction D1. The circuit board A3 is a flat and straight board extending only in a single direction, and on the circuit board A3 are disposed the light source A5 and a photosensitive element A6. Before the circuit board A3 deforms, the light source A5 and the photosensitive element A6 are all disposed in the vertical direction D1, as shown in FIG. 2.

When in assembly, the circuit board A3 are disposed between the lower and upper housings A1, A2, then the two housings A1, A2 are clamped together in the vertical direction D1 to make the bending frame A22 of the upper housing A2 and a separating frame A12 of the lower housing A1 press the circuit board A3 from both sides, so that the circuit board A3 is bent 180 degrees, in such a manner that the photosensitive element A6 is located right in front of the separating frame A12 and changed to be disposed in a horizontal direction D2 perpendicular to the vertical direction D1, the light source A5 is also changed to be disposed in the horizontal direction D2, and the lens A4 is located in the horizontal direction D2 adjacent to the photosensitive element A6 to shoot in the horizontal direction D2, as shown in FIG. 3.

The endoscope A is assembled in the vertical direction D1, and the circuit board A3 is bent 180 degrees during assembly to change the direction in which the photosensitive element A6 and the light source A5 were originally disposed from the vertical direction D1 to the horizontal direction D2. However, the endoscope A has the following disadvantages:

First of all, the circuit board A3 is a precision electronic component and will be very likely to be ruptured after being bent 180 degrees, which results in a low yield rate. Besides, the photosensitive element A6 and the light source A5 on the circuit board A3, during assembly, change in orientation from the vertical direction D1 to the horizontal direction D2, which improves ease and efficiency of assembly.

The present invention has arisen to mitigate and/or obviate the afore-described disadvantages.

SUMMARY OF THE INVENTION

The primary object of the present invention is to provide an endoscope with a T-shaped flexible circuit board, wherein the T-shaped flexible circuit board cooperates with the base mounting frame to better fit into a pipe of the endoscope, so as to improve the ease of assembly. Further, the flexibility of the circuit board reduces the volume of the endoscope and improves applicability.

To achieve the above object, an endoscope with a T-shaped flexible circuit board in accordance with the present invention comprises: an endoscope with a T-shaped flexible circuit board comprising;

a base mounting frame with two arm portions and a connecting portion connected between one ends of the two arm portions, between another ends of the two arm portions being defined a gap, each of the two arm portions extending from the connecting portion to the gap and having a length, a surface of the base mounting frame located between the two arm portions and the connecting portion being defined as an inner surface, and another surface opposite the inner surface being defined as an outer surface of the base mounting frame, each of the two arm portions having an end surface which extends in a forward direction;

the T-shaped flexible circuit board including a mounting portion electrically connected to an electric connecting portion, the mounting portion and the electric connecting portion defining a non-zero angle with respect to each other, the T-shaped flexible circuit bard including a mounting surface and a connecting surface, the connecting surface being abutted against the inner surface of the base mounting frame in such a manner that the mounting portion is abutted against the end surfaces, the arm portions and the connecting portion of the base mounting frame, and the electric connecting portion bridges over the connecting portion and extends out of the base mounting frame to electrically connect a power supply or an imaging device;

a photosensitive element electrically connected to the mounting portion of the flexible circuit board and mounted on the mounting surface;

two light emitting elements being electrically connected to the mounting portion of the flexible circuit board, located in alignment with the end surfaces of the arm portions of the base mounting frame, and disposed in the forward direction; and a camera including a lens at one end and an engaging groove at another end thereof, and having a length larger than the length of the arm portions, the camera being disposed on the mounting surface of the mounting portion of the flexible circuit board in such a manner that the camera is disposed in a space defined by the two arm portions and the connecting portion of the base mounting frame, the photosensitive element is engaged in the engaging groove, the lens of the camera protrudes out of the gap between the arm portions of the base mounting frame and is disposed in the forward direction, and the camera is disposed in the forward direction and protrudes out of the end surfaces of the base mounting frame and also protrudes out of the two light emitting elements.

The photosensitive element, the two light emitting elements and the camera are mounted onto the T-shaped flexible circuit board, then the flexible circuit board deforms to fit in the base mounting frame. During assembly, the photosensitive element, the two light emitting elements and the camera are maintained in the same orientation, and the T-shaped flexible circuit can be pushed into the base mounting frame simply by applying a force in a single direction parallel to the orientation direction of the photosensitive element, the two light emitting elements and the camera. Therefore, the assembly precision of the endoscope is easy to control, so as to improve the product accuracy.

DETAILED DESCRIPTION OF THE PREFERRED EMBODIMENTS

Figure 1:
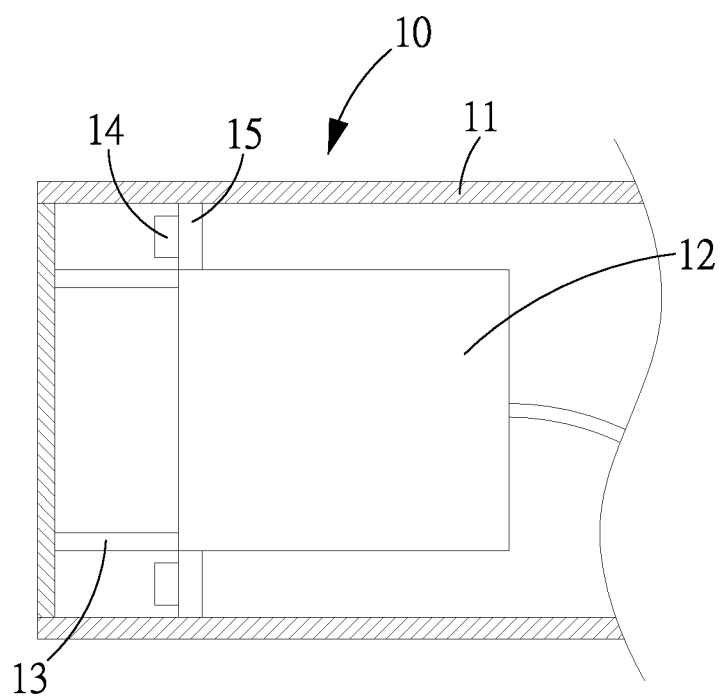
FIG. 1 is a cross sectional view of a conventional endoscope.
Figure 2:
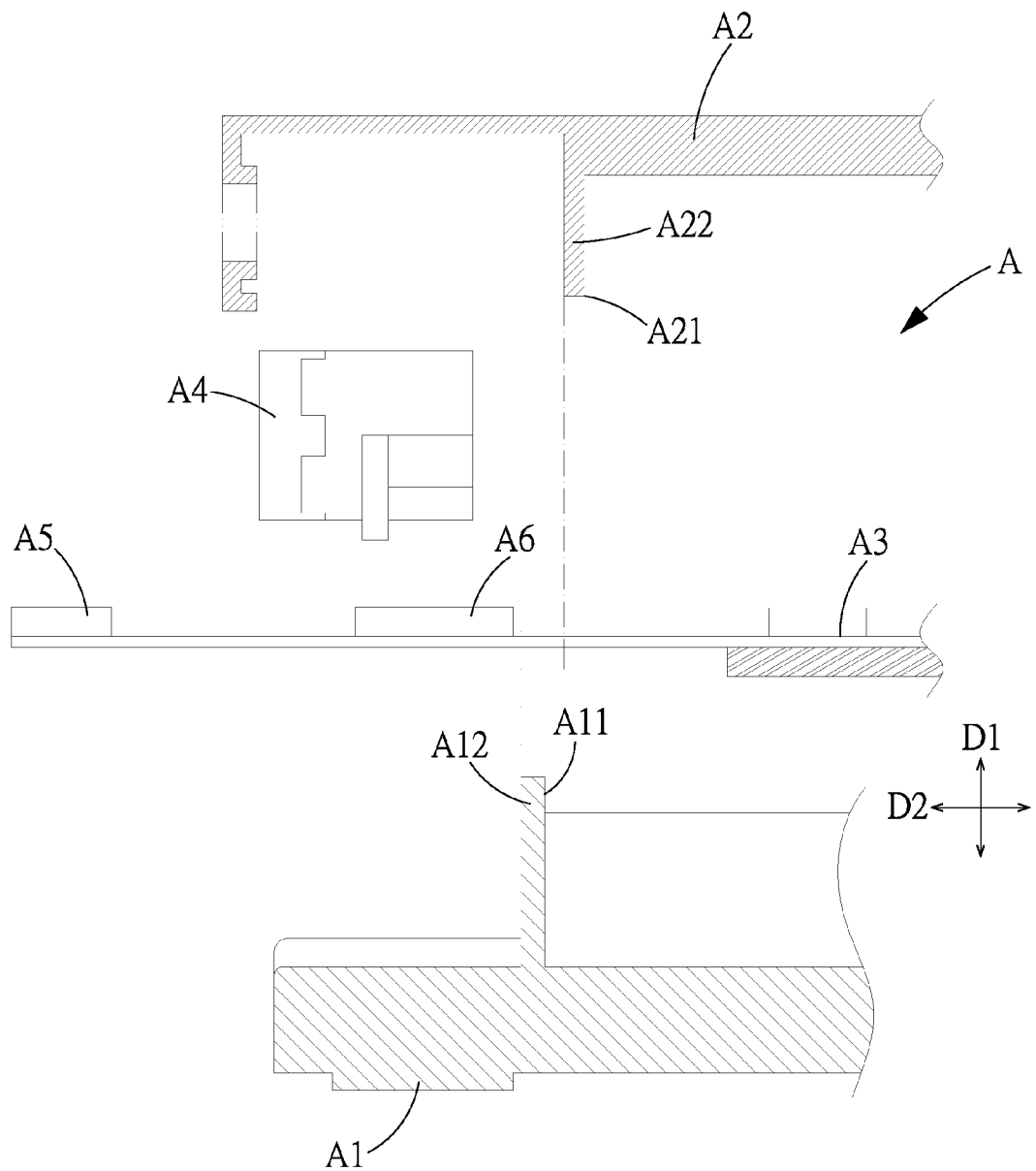
FIG. 2 shows a conventional endoscope before assembly.
Figure 3:
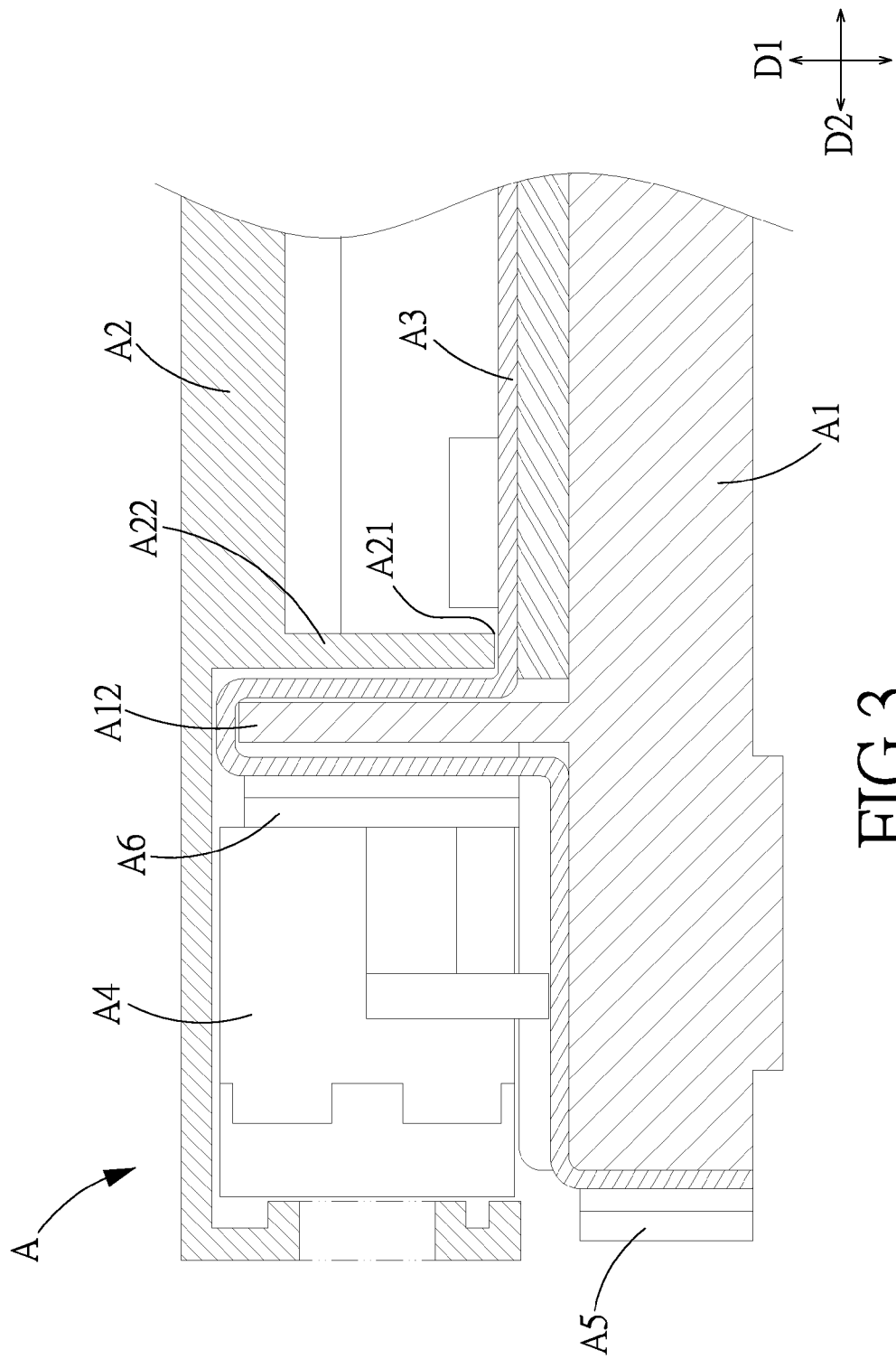
FIG. 3 shows the conventional endoscope of FIG. 2 after assembly.
Figure 4:
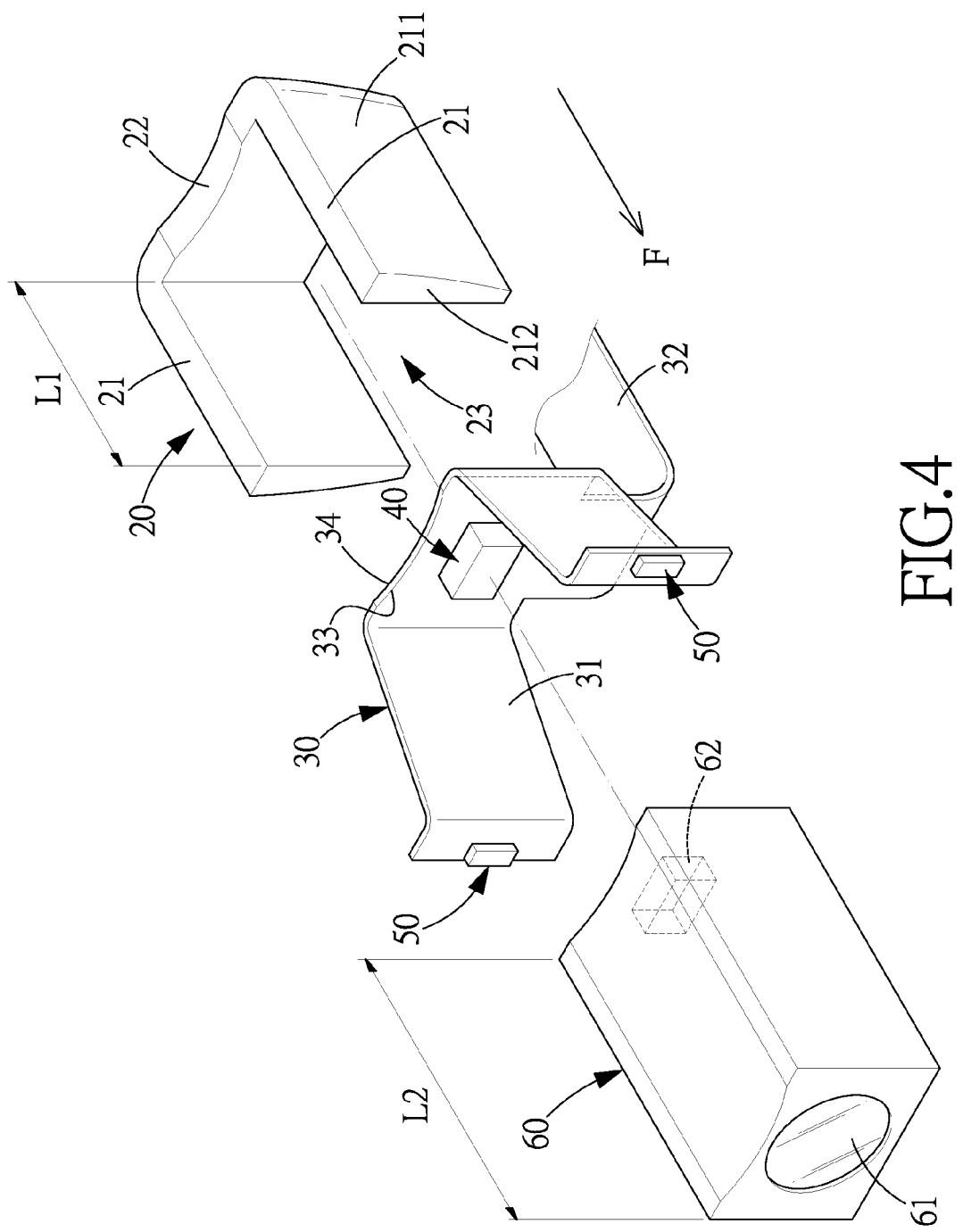
FIG. 4 is an exploded view of an endoscope with a T-shaped flexible circuit board in accordance with a preferred embodiment of the present invention.

The present invention will be clearer from the following description when viewed together with the accompanying drawings, which show, for purpose of illustrations only, the preferred embodiment in accordance with the present invention.

Referring to FIGS. 4-7, an endoscope with a T-shaped flexible circuit board 30 in accordance with a preferred embodiment of the present invention comprises: a base mounting frame 20, the T-shaped flexible circuit board 30, a photosensitive element 40, two light emitting elements 50 and a camera 60.

The base mounting frame 20 is a U-shaped structure which includes two arm portions 21 and a connecting portion 22 connected between one ends of the two arm portions 21. Between another ends of the two arm portions 21 is a gap 23, and the two arm portions 21 extend from the connecting portion 22 to the gap 23 and each have a length L1.

A surface of the base mounting frame 20 located between the two arm portions 21 and the connecting portion 22 is defined as an inner surface, and another surface opposite the inner surface is defined as an outer surface of the base mounting frame 20. Each of the two arm portions 21 has an arc-shaped outer surface 211 and an end surface 212 which extends in a forward direction F.

Figure 5:
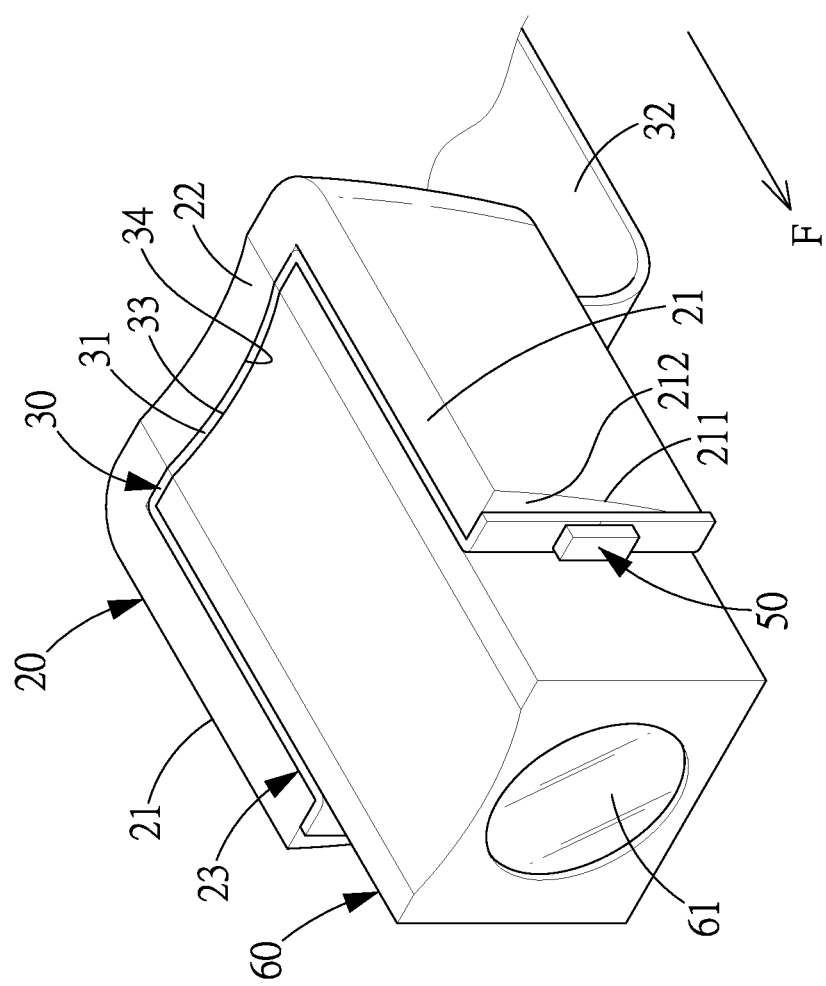
FIG. 5 is an assembly view of the endoscope with a T-shaped flexible circuit board in accordance with the present invention.
Figure 6:
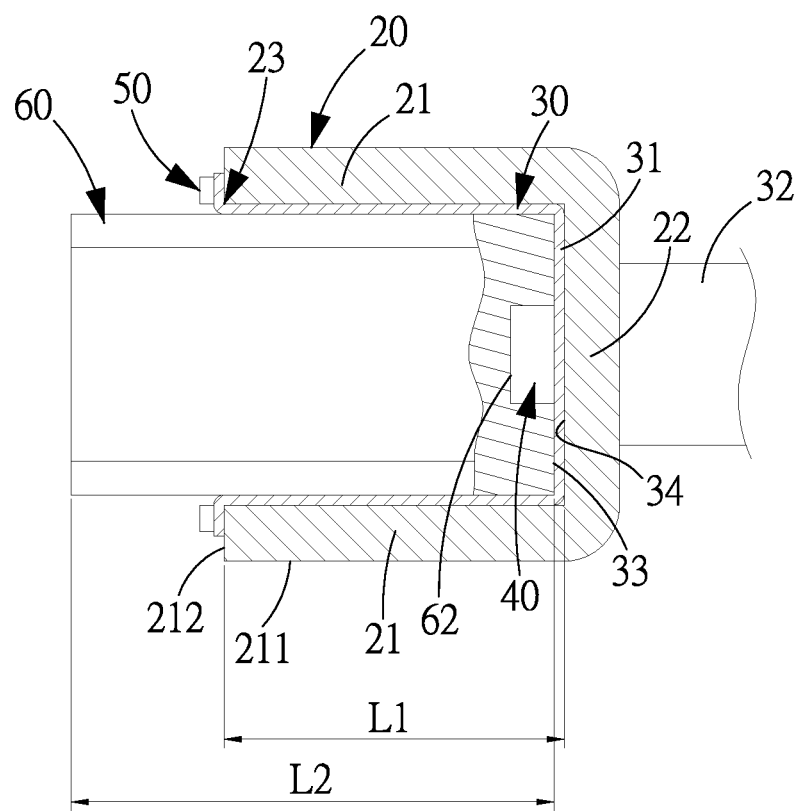
FIG. 6 is a cross sectional view of the endoscope with a T-shaped flexible circuit board in accordance with the present invention.
Figure 7:
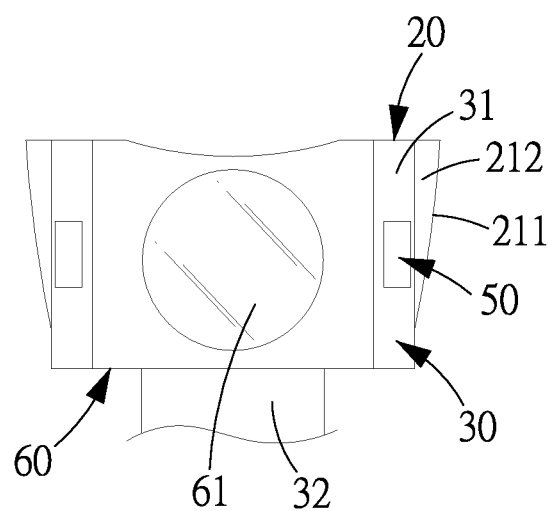
FIG. 7 is front side view of the endoscope with a T-shaped flexible circuit board in accordance with the present invention.

The T-shaped flexible circuit board 30 includes a mounting portion 31 electrically connected to an electric connecting portion 32. The T-shaped flexible circuit board 30 is deformable, and the mounting portion 31 and the electric connecting portion 32 define a non-zero angle with respect to each other. In this embodiment, the mounting portion 31 is electrically connected to the electric connecting portion 32 in a perpendicular manner, so as to form a T-shaped structure. The T-shaped flexible circuit bard 30 includes a mounting surface 33 and a connecting surface 34. When in assembly, as shown in FIG. 5, the mounting portion 31 deforms to make the connecting surface 34 abutted against the inner surface of the base mounting frame 20 in such a manner that the mounting portion 31 is abutted against the end surfaces 212, the arm portions 21 and the connecting portion 22 of the base mounting frame 20, and the electric connecting portion 32 bridges over the connecting portion 22 and extends out of the base mounting frame 20 to electrically connect a power supply or an imaging device (not shown).

The photosensitive element 40 is electrically connected to the mounting portion 31 of the flexible circuit board 30 and mounted on the mounting surface 33 and located in alignment with the connecting portion of the base mounting frame 20.

The two light emitting elements 50 are electrically connected to two ends of the mounting portion 31 of the flexible circuit board 30, located in alignment with the end surfaces 212 of the arm portions 21 of the base mounting frame 20, and disposed in the forward direction F.

The camera 60 includes a lens 61 at one end and an engaging groove 62 at another end thereof, and has a length L2 larger than the length L1 of the arm portions 21. The camera 60 is disposed on the mounting surface 33 of the mounting portion 31 of the flexible circuit board 30 in such a manner that the photosensitive element 40 is engaged in the engaging groove 62, the lens 61 of the camera 60 protrudes out of the gap 23 between the arm portions 21 of the base mounting frame 20 and is disposed in the forward direction F, so that the camera 60 is disposed in the forward direction F and protrudes out of the end surfaces 212 of the base mounting frame 20 and also protrudes out of the two light emitting elements 50.

When manufacturing the endoscope with the T-shaped flexible circuit board 30 in accordance with the present invention, the photosensitive element 40, the light emitting elements 50 and the camera 60 are electrically connected to and mounted on the flexible circuit board 30, then the photosensitive element 40, the light emitting elements 50 and the camera 60 are disposed in the forward direction F. At this moment, the T-shaped flexible circuit 30 can be pushed through the gap 23 into the space defined by the two arm portions 21 and the connecting portion 22 of the base mounting frame 20 simply by applying a force in a single direction parallel to the forward direction F, so that the T-shaped flexible circuit board 30 will deform to conform to and abut against the inner surface of the base mounting frame 20. By such arrangements, the base mounting frame 20 can carry all the parts, including the flexible circuit board 30, the photosensitive element 40, the light emitting elements 50 and the camera 60. Applying a force in a single direction parallel to the forward direction F (the orientation direction of the flexible circuit board 30, the photosensitive element 40, the light emitting elements 50 and the camera 60) considerably improves ease and efficiency of assembly.

The photosensitive element 40, the light emitting elements 50 and the lens 61 of the camera 60 are still maintained in the forward direction F after assembly, namely, the orientation direction of the flexible circuit board 30, the photosensitive element 40, the light emitting elements 50 and the camera 60 does not change through the whole assembly process, so that the assembly precision of the endoscope is easy to control, so as to improve the product accuracy.

Furthermore, the base mounting frame 20 is a U-shaped structure defined by the two arm portions 21 and the connecting portion 22, the mounting portion 31 of the T-shaped flexible circuit board 30 deforms slightly to conform to the shape of the base mounting frame 20 without substantial bending, which prevents the T-shaped flexible circuit board 30 from rupture during the assembly process, thus improving the yield rate of the T-shaped flexible circuit board 30.

Finally, the mounting frame 20 carrying all the parts can be assembled in a pipe (not shown) to form an endoscope, which greatly improves the ease of assembly, and consequently reducing the labor cost required for assembly.

Besides, the T-shaped flexible circuit board 30 is flexible, so it can be closely abutted against the inner surface of the base mounting frame 20, thus avoiding unnecessary increase in volume of the endoscope. The circuit board 30 is flexible to fit the bending shape of the base mounting frame 20, and the base mounting frame 20 is designed to adapt to different pipes, namely, the flexibility of the circuit board 30 improves applicability. Moreover, the outer surfaces 211 of the arm portions 21 of the base mounting frame 20 are arc-shaped to better fit into the normally circular-shaped pipe (not shown) of an endoscope.

On the other hand, the flexible circuit board 30 is abutted against the base mounting frame 20, the light emitting elements 50 are aligned with the end surfaces 212 of the arm portions 21 of the base mounting frame 20, and the camera 60 protrudes out of the end surfaces 212 of the arm portions 21 of the base mounting frame 20, namely, the lens 61 of the camera 60 is located in front of the light emitting elements 50. By such arrangements, the camera 60 itself can block the light of the light emitting elements 50 from reaching the lens 61, so the endoscope of the present invention doesn't require the use of a light shield, which reduces material cost required for production.

While we have shown and described various embodiments in accordance with the present invention, it is clear to those skilled in the art that further embodiments may be made without departing from the scope of the present invention.

What is claimed is:

1. An endoscope comprising:
   a base mounting frame comprising a unitary structure including a connecting portion, a first arm portion, and a second arm portion, the first arm portion connected to and abutting a first edge of the connecting portion and the second arm portion connected to and abutting a second edge of the connecting portion opposite the first edge, with the first arm portion facing the second arm portion;
   a flexible circuit board including a first arm portion, a second arm portion, and a connecting portion connecting the first arm portion and the second arm portion, the first arm portion, the second arm portion, and the connecting portion of the flexible circuit board having planar surfaces spaced apart by a thickness of the flexible circuit board and positioned parallel to, respectively, planar surfaces of the first arm portion, the second arm portion, and the connecting portion of the base mounting frame;
   a light emitting element electrically connected to the first arm portion of the flexible circuit board;
   a second light emitting element electrically connected to the second arm portion of the flexible circuit board; and
   a camera including a lens mounted thereon and a photosensitive element electrically connected to the flexible circuit board and adjacent to the connecting portion of the base mounting frame, the camera disposed in a space defined by the first arm portion, the second arm portion, and the connecting portion of the flexible circuit board,
   wherein the camera and the connecting portion of the base mounting frame are separated in the longitudinal direction by a distance substantially equal to the thickness of the connecting portion of the flexible circuit board.

2. An endoscope as in claim 1, wherein the planar surfaces of the first arm portion of the flexible circuit board lay flat against the first arm portion of the base mounting frame and the camera, respectively, and the planar surfaces of the second arm portion of the flexible circuit board lay flat against the second arm portion of the base mounting frame and the camera, respectively.

3. An endoscope as in claim 1, wherein a plane passing through the first arm portion of the base mounting frame intersects the light emitting element.

4. An endoscope as in claim 1, wherein the first arm portion and the second arm portion of the flexible circuit board are positioned between the camera and the first arm portion and the second arm portion, respectively, of the base mounting frame substantially without gaps therebetween.

5. An endoscope as in claim 1, further comprising a pipe, the camera and the base mounting frame received by the pipe, wherein the first arm portion and the second arm portion of the base mounting frame each comprises an outer surface arc-shaped to match an internal surface of the pipe and reduce a volume of the endoscope.

6. An endoscope as in claim 1, wherein the base mounting frame has a height perpendicular to the first edge which is substantially equal to the width of the first arm portion of the flexible circuit board.

7. An endoscope as in claim 1, wherein the connecting portion of the flexible circuit board is substantially coextensive with the connecting portion of the base mounting frame.

8. An endoscope as in claim 1, wherein the first arm portion abuts a first edge of the connecting portion and the second arm portion abuts a second edge of the connecting portion opposite the first edge, with the first arm portion facing the second arm portion, and wherein the connecting portion, the first arm portion, and the second arm portion form the unitary structure before, and to, facilitate assembly of the endoscope.

9. An endoscope as in claim 8, wherein the planar surfaces lay flat against the base mounting frame and the camera, respectively.

10. An endoscope as in claim 8, wherein a plane passing through the first arm portion of the base mounting frame intersects the first light emitting element.

11. An endoscope as in claim 8, wherein the flexible circuit board is positioned between the camera and the base mounting frame substantially without a gap therebetween.

12. An endoscope as in claim 8, wherein the light emitting element and the second light emitting element are positioned along a length of the camera between the lens and the photosensitive element.

13. A method of making an endoscope, the method comprising:

electrically connecting a photosensitive element to a connecting portion of a flexible circuit board, a light emitting element to a first arm portion of the flexible circuit board, and a second light emitting element to a second arm portion of the flexible circuit board, the first arm portion, the second arm portion, and the connecting portion of the flexible circuit board having planar surfaces spaced apart by a thickness of the flexible circuit board;

flatly abutting a base mounting frame comprising a unitary structure to the flexible circuit board, the base mounting frame including a connecting portion, a first arm portion, and a second arm portion, the first arm portion connected to and abutting a first edge of the connecting portion and the second arm portion connected to and abutting a second edge of the connecting portion opposite the first edge, with the first arm portion facing the second arm portion, the first arm portion, the second arm portion, and the connecting portion of the flexible circuit board positioned parallel to, respectively, planar surfaces of the first arm portion, the second arm portion, and the connecting portion of the base mounting frame;

positioning a camera in a space defined by the first arm portion, the second arm portion, and the connecting portion of the flexible circuit board until the camera and the connecting portion of the base mounting frame are separated in the longitudinal direction by a distance substantially equal to the thickness of the connecting portion of the flexible circuit board, the camera comprising a lens and the photosensitive element.

14. A method as in claim 13, wherein the planar surfaces of the first arm portion and the second arm portion of the flexible circuit board lay flat against the first arm portion and the second arm portion of the base mounting frame, respectively, and the camera.

15. A method as in claim 13, wherein the first arm portion and the second arm portion of the flexible circuit board are positioned between the camera and the first arm portion and the second arm portion, respectively, of the base mounting frame substantially without gaps therebetween.

* * * * *